BEST AVAILABLE COPY
M. Mattson,
Syringe.
No. 3,106. Reissued Sep. 1, 1868.
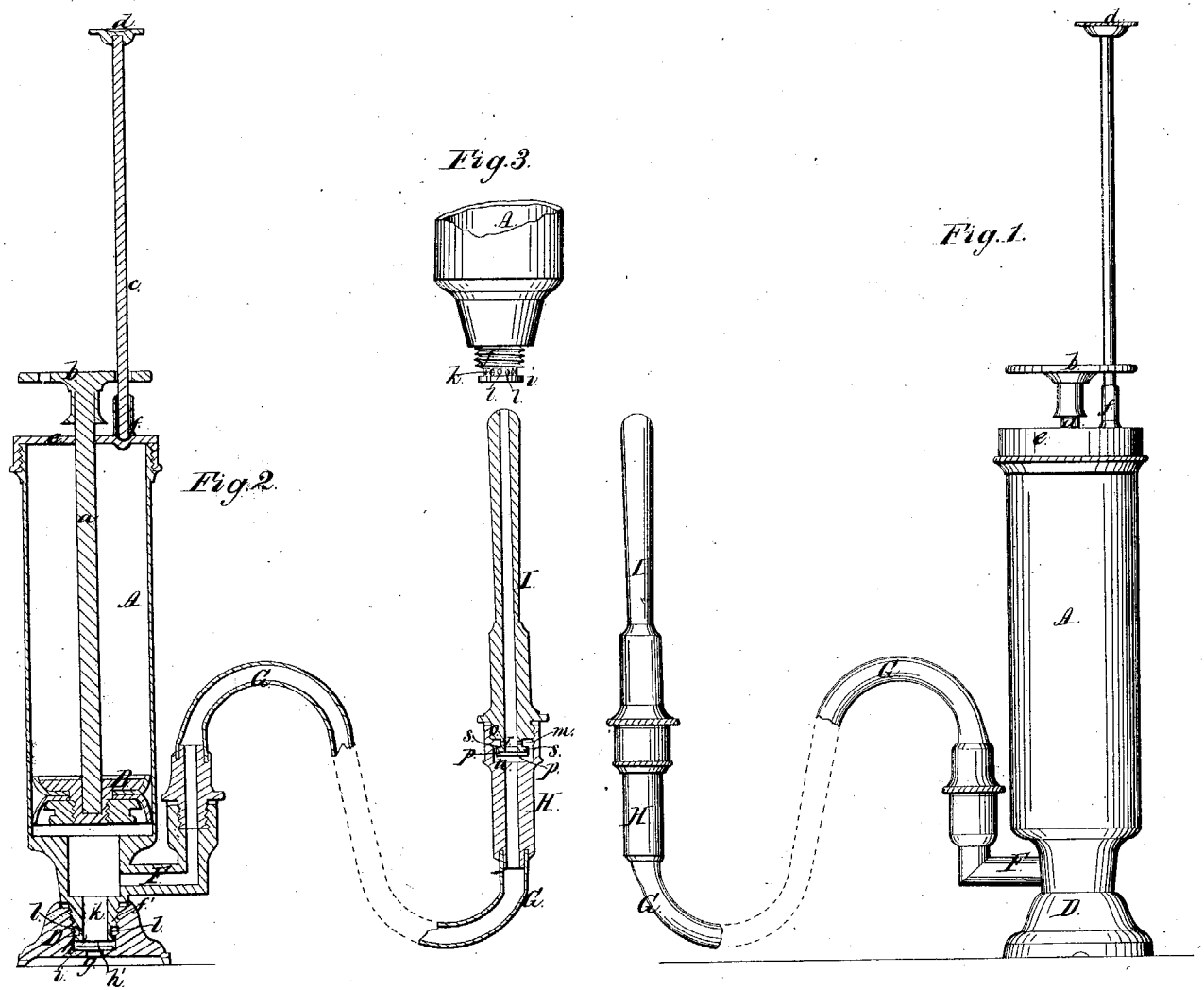
N. PETERS, PHOTO-LITHOGRAPHER, WASHINGTON, D. C.

United States Patent Office.

MORRIS MATTSON, OF NEW YORK, N. Y.

*Letters Patent No.* 10,742, *dated April* 4, 1854; *extended seven years; reissue No.* 3,106, *dated September* 1, 1868.

IMPROVEMENT IN ENEMA-SYRINGES.

The Schedule referred to in these Letters Patent and making part of the same.

TO ALL WHOM IT MAY CONCERN:

Be it known that I, MORRIS MATTSON, M. D., formerly of Boston, Massachusetts, now of the city of New York, in the county of New York, and State of New York, have invented certain new and useful Improvements in Enema-Syringes; and I do hereby declare that the following is a full, clear, and exact description thereof, and of their mode or manner of operation, reference being had to the accompanying drawings, and to the letters of reference marked thereon, and making a part of this specification.

By means of my improvements, I am enabled to produce a syringe which is more easily operated by the patient or user, which is more certain and effective in its action, and which entirely prevents the fluid being injected from being forced back from the bowels into the syringe.

Figure 1 is an elevation or perspective view of a syringe containing my improvements.

Figure 2 is a longitudinal and central section of fig. 1.

Figure 3 is an external view of the lower part of the pump-barrel.

In the construction of a syringe, such as is represented in the drawings, I employ a pump-barrel, A, having a piston, B, adapted to it. To the rod *a* of such piston is fixed a head, *b*, which is cut away or perforated to receive or permit the passage through it of a rod, *c*, which terminates at its top or upper end in a button or head, *d*, and which is fixed to the screw-cap *e* of the barrel B, or rests in a socket, *f*, attached to such cap.

This rod *c*, or its equivalent, may be termed the thumb-rest, as its purpose is to afford a support for the thumb or finger of a person's hand as the piston-rod and piston are being elevated by the application or upward pressure of one or two other fingers of the same hand. The instrument is also held down on whatever it may rest by such pressure on the head *d* of the rod *c*.

By means of such thumb-rest, the syringe, when a barrel-syringe, and having a piston working therein, can be readily worked with one hand, while the other hand is left free to hold the terminal or injecting-tube I in place within the rectum. When the instrument is not being used, the thumb-rest or rod *c* may be removed or detached from the barrel and packed up in the box or case which usually accompanies an instrument of this nature.

The lower end of the pump-barrel B is screwed to a broad base, D, by a screw, *f*, or otherwise firmly secured thereto. Through the bottom of this base an ingress-tube or opening, *g*, is made, which connects with a valve-chamber, *h*, formed within the base, and below the screw *f*, and around the lower end of the pump-barrel. In such valve-chamber, and over the hole or opening *g*, there is placed a small circular disk, *h'*, of prepared rubber or other suitable material, the diameter of such disk being a little less than that of the chamber in which it is placed, and the chamber being also of a depth somewhat greater than the thickness of the valve, so that the valve or disk can freely vibrate therein.

Above the disk or valve *h'*, and connected with the lower end of the male screw on the pump-barrel, is a circular ring-valve stop or seat, *i*, of an external diameter equal or about equal to that of the valve, and connected to the screw by a short tube, K, whose sides are perforated to allow the passage of liquid through them, such perforations being seen at *l l*, figs. 2 and 3.

When the piston is raised, the disk or valve *h'* will be drawn up against the seat *i*, and the liquid will flow in through the ingress-hole *g*, and upward and against the bottom of the valve, and around its edges and the seat *i*, and through the perforations *l l*, into the barrel of the piston. When the piston is depressed or forced down, the valve will be forced or pressed down on its seat at the bottom of the chamber *h*, and will thus close the ingress-hole and prevent the escape of the liquid through such hole, and such fluid will then be forced into and through the exit or discharge-tube F, opening from the lower part of the barrel B. I am thus enabled to make use of, as and for a valve, of a single disk, and without the necessity of a hinge, or any connection of it to the surrounding parts.

The action and character of the disk or valve *h'*, under the varying circumstances of its use, are important, as such valve will close, under the return of the pressure, sooner than a ball or any other metallic or other valve having a backward-and-forward movement only can do, and consequently the working-barrel of the instrument is filled at once without the admission of air. Such valve, from its elastic nature, will also readily adapt itself to any irregularities of surface in the chamber in which it plays, whether irregularities produced by workmanship or arising from the lodgment of suspended matter in the fluid used, and will close tightly, notwithstanding such irregularities. Such form of valve will also act equally well in all positions of the syringe, and can be applied to and used in connection with syringes of other construction than having a barrel and piston.

To the exit or discharge-tube or pipe F, a flexible tube, G, is screwed or otherwise properly connected, to the other end of which is fixed a socket-tube, H, which is intended to receive the jet-pipe or injecting-tube I, which is shown as screwed into it, as at O, fig. 2. Such socket-tube is provided with a valve-chamber, *m*, a valve-seat, *n*, and a disk-valve, *p*, and in the screw part of the injecting-tube is a short perforated tube, *r*, and a circular valve-seat, *s*, the whole and its several parts being like those before described in connection with the pump-barrel B.

The particular mechanical construction and form of the valve-chamber, valve-seat, and perforated tube are of course not material, as all the several parts may be varied and without changing the action of the disk-valve. In many cases the fluid, which is injected into the bowels, is forced back into the syringe-tube by the contraction of the rectum. This is very objectionable, and to be prevented as far as possible, as the fluid thus forced back has been rendered offensive by the addition of fœcal or excremental matter, and this soon renders the syringe disgusting, and when the terminal tube is withdrawn from the rectum any fluid that may be in it is liable to flow out upon the floor, carpet, or other furniture, unless some means is provided to prevent it. Hence the importance of placing the injecting-valve, or the valve connected with the injecting-tube, at the extremity of it most distant from the pump-barrel or forcing-mechanism, instead of having such valve placed at the end of such tube nearest the barrel or forcing-mechanism.

As will be at once apparent, by so placing the injecting-valve at the farther end of the flexible tube, as described, all backward flow of the injected fluid into the flexible tube or beyond the terminal or injecting-tube or pipe I is wholly prevented, and the instrument is thus kept free from all fœcal or excremental matter, and when the pipe I is withdrawn from the rectum, only a very small quantity of fluid can be brought out with it.

What I claim as my invention, and desire to secure by Letters Patent, is—

1. The combination of the thumb or finger-rest *d* with the barrel and piston for the purpose set forth.

2. The combination of the elastic or floating disk or valve *h'*, with its seat and chamber, arranged and operating substantially as described.

3. Placing the ejection or outlet-valve of a syringe at or near the extremity of the discharge or injecting-tube most distant from the pump-barrel, or its equivalent, for the purposes set forth.

MORRIS MATTSON.

Witnesses:

S. D. LAW,

FRED. B. SEARS.